United States Patent [19]

Kass

[11] Patent Number: 5,407,794
[45] Date of Patent: Apr. 18, 1995

[54] OXAZINE STAINED LYMPHOCYTES AND METHOD

[75] Inventor: Lawrence Kass, Hinckley, Ohio

[73] Assignee: Cytocolor Inc., Hinckley, Ohio

[21] Appl. No.: 194,217

[22] Filed: Feb. 9, 1994

Related U.S. Application Data

[63] Continuation-in-part of Ser. No. 942,037, Sep. 8, 1992, abandoned.

[51] Int. Cl.⁶ .............................................. G01N 33/48
[52] U.S. Cl. ......................................... 436/63; 424/3; 424/7.1; 424/722; 435/2; 435/240.2
[58] Field of Search ........................... 435/1, 34, 29, 2; 436/63; 424/93 V, 722, 93 AA, 3, 7.1

[56] References Cited

U.S. PATENT DOCUMENTS

| | | | |
|---|---|---|---|
| 4,376,820 | 3/1983 | Gianinni et al. | 435/4 |
| 4,400,370 | 8/1983 | Kass | 424/3 |
| 4,500,509 | 2/1985 | Kass | 424/3 |

OTHER PUBLICATIONS

Sigma 1990, "Biochemicals Organic Compounds . . ." p. 1496.
American Journal of Clinical Pathology 88:436–441, 1987. "Identification of Neutrophils . . . "Kass.
Rapid Identification of T Helper and T Cytotoxic/Suppressor Lymphocytes with Oxazine Dye Lawrence Kass Departments of Pathology and Medicine, Case Western Reserve University School of Medicine, Cleveland, Ohio 44109 1052-0295/93/68-05-247/$3.00/0 Biotechnic & Histochemistry Copyright ©1993 by Williams & Wilkins vol. 68 No. 5 published Oct. 4, 1993 pp. 247–254.

*Primary Examiner*—Jeffrey R. Snay
*Assistant Examiner*—Rachel Freed

[57] ABSTRACT

Peripheral blood lymphocytes displayed a plurality of sizes and colors when exposed first to a fixative solution of C.I. basic blue 141, then to an aqueous alkaline solution of the same dye and subsequently treated with a neutral HEPES buffer solution containing small but effective amounts of various metal compounds. As confirmed with purified lymphocyte subpopulations obtained with a cell sorter, T helper cells (CD4) were small and their nuclei and cytoplasm stained deep blue. T cytotoxic/suppressor cells (CDS) were larger than T helper cells, their nuclei stained pale green or blue green and their cytoplasm contained a cluster of magenta colored granules. Used in the process described, basic blue 141 provides means of identifying and differentiating CD4 and CD8 cells under the ordinary light microscope without using monoclonal antibodies or fluorescence.

10 Claims, No Drawings

OXAZINE STAINED LYMPHOCYTES AND METHOD

PRIOR APPLICATIONS

This application is a continuation-in-part of application Ser. No. 07/942,037 filed on Sep. 8, 1992, now abandoned.

BACKGROUND OF THE INVENTION

This invention is directed to stained lymphocytes and a method of preparing same by using a single, substantially pure oxazine dye for the cytological preparation of a biopsy specimen of hematopoietic origin. More specifically, this invention relates to the use of a single oxazine dye for differentiating, identifying and enumerating lymphocytes among a plurality of cells of hematopoietic origin selected from the group consisting of blood cells, bone marrow cells and lymph node cells. Peripheral blood lymphocytes displayed a plurality of sizes and colors when exposed first to a fixative solution of an oxazine dye (C.I. basic blue 141), then to an aqueous alkaline solution of the same dye and subsequently rinsed in a neutral HEPES buffer containing small but effective amounts of various metal compounds. Purified lymphocyte subpopulations obtained with a cell sorter, showed that T helper cells (CD4) were small and their nuclei and cytoplasm stained deep blue. T cytotoxic/suppressor cells (CDS) were larger than T helper cells, their nuclei stained pale green or blue green and their cytoplasm contained a cluster of magenta colored granules. Used in the manner described, basic blue 141 is a means of identifying and differentiating CD4 and CD8 cells under the ordinary light microscope without using monoclonal antibodies or fluorescence.

In the prior art, there are various known methods for counting and classifying leukocytes. For example, the cytotechnician microscopically views a biopsy specimen prepared on an ordinary microscope slide that has been stained with Romanowsky stains. The cytotechnician examines the stained leukocytes and classifies them according to cell type. This method, however, is time consuming and has the disadvantage of not being reliable with respect to counting and classifying the less abundant cells. In a typical automated system, a biopsy specimen is stained in the usual manner with a Romanowsky stain and then scanned mechanically under a microscope provided with an electronic image tube. When the leukocyte comes in view of the image tube, the slide is stopped. An image analyzing computer connected to the image tube classifies the leukocyte according to its cell profile and cytoplasm color. Again the system has the disadvantage of being time consuming and costly. The use of a single specific oxazine dye (BB141) is an improvement over the Romanowsky stains even though mixtures of dyes are still the basis for morphological hematology and are being used for the identification of cells. The mixture of dyes produces the Romanowsky effect defined as a condition wherein the coloration of the cell components results from the combined action of the mixture which cannot be produced by either dye acting alone. The state of the art fails to teach the use of a single, substantially pure, commercially available stain capable of panoptically and metachromatically staining lymphocyte subpopulations in a biopsy specimen.

The identification of lymphocytes and their various subpopulations has become more important and interesting to biomedical researchers especially for diagnostic purposes. More particularly, the subpopulations of lymphocytes have been better defined and their functions in the immune system have become more clearly delineated. The important subpopulations include the B-cells, T-helper cells, T-suppressor cells, and Natural Killer (NK) cells. The B-cells are believed to be bursa derived and are involved in the synthesis of circulating immunoglobulins. The T-helper and T-suppressor cells are involved in the modulation of the immune response and in the regulation of erythropoiesis. More important, the Natural Killer cells represent the body's first line of defense against malignancy, since these cells are cytotoxic to foreign cells, and do not require the mediation of complement to effect their lysis.

In recent years the function and complexity of the T-helper and T-suppressor cell populations have received an increasing amount of attention. It is believed that the HTLV-I virus is the specific etiologic agent for adult T-cell leukemia. This virus specifically attacks the T-helper cell by entering the genetic material and "immortalizes" the cell, transforming it into a large leukemic lymphoblast with striking convolutions and indentations of the nucleus and contain a large nucleolus. The HTLV-I virus particles replicate within the T-helper cell and enter into the circulation system to infect other T-helper cells.

In contrast to the "immortalization" of the T-helper cell in the HTLV-I virus infestation, the HTLV-IV virus infects the T-helper cells specifically and in so doing destroys the cells. The HTLV-IV virus is known to be the specific causative agent of the acquired immune deficiency syndrome (AIDS). In this disorder (AIDS), it was found that the number of T-helper cells is greatly diminished because of the lethal effects of the virus, leading to a reversal of the ratio between the T-helper cell and the T-suppressor cell. Moreover, information about the antibodies to the HTLV-IV virus, and the ratio of the T-helper to the T-suppressor cells is a valuable diagnostic test for determining the presence of HTLV IV infection, and also for confirming the diagnosis of AIDS.

In the prior art, Kass teaches that the identification of T-cells and B-cells and other lymphocyte subpopulations can be accomplished by using a single organic dyestuff; see U.S. Pat. Nos. 4,400,370; 4,500,509; 4,581,223; 4,615,878; 4,714,606; 4,810,487; 4,853,210; and 5,106,744. The Kass patents disclose that Basic Orange 21 is a supravital stain and therefore must be used on living blood cells in a liquid suspension viewed in the presence of absorbance or fluorescent light. Kass also teaches that Basic Blue 41 dye, however, must be used on a fixed biopsy specimen. Here the lymphocyte subpopulations were identified on the basis of the difference in the intensity of staining and the caliber of the nuclear chromatin strands in the nucleus, as well as the presence of metachromatically staining granules in the cytoplasm.

More specifically, the differences in size and coloration of lymphocytes using mixtures of dyes have been known for nearly a century. In 1910 and 1911, Pappenheim described and illustrated lymphocytes in great detail; see Pappenheim, A., Ueber verschiedenen Typen yon Lymphozyten und Monozyten, zumm Teil im scheinbar normalen Blut; Folia Haematologica 12:26–38, 1911 and Pappenheim, A., Ferrata, A. Ueber die verschiedenen lymphoden Zellformen des normalen und pathologischen Blutes, Folia Haematol 10:78-92, 1910. Ehrlich and Lazarus described several types of lymphocytes that displayed differential coloration with the triacid staining mixture composed of methyl green, acid orange G and acid fuchsin; see Ehrlich, P. and Lazarus, A. Anemia, Histology of the blood, normal and pathologic; In Diseases of the Blood, A. Stengel, Ed. W. B. Saunders, Philadelphia. pp. 17-150, 1905. Illustrations from their chapter in Nothnagel's 1905 textbook display small lymphocytes that show dark blue staining of nucleus and cytoplasm, and other lymphocytes that are larger and stain pale green. Although Ehrlich did not speculate as to the functional significance of these different types of lymphocytes, he astutely observed that lymphocytes were not all the same. Some were large, some were small, some stained darkly and others stained pale.

More recently, identification of subpopulations of lymphocytes in specimens of blood, bone marrow, and lymph nodes has become a standardized and routine procedure in many hematology and immunopathology labs. Using monoclonal antibodies, these populations were originally characterized as T helper and T suppressor cells, reflecting their functions in the immune response. Increasingly, additional subpopulations have been identified and characterized. Based upon their surface marker characteristics, some of these subpopulations include lymphocytes having both HLADR and CD8 markers, NK or natural killer cells, and cytotoxic suppressor cells. As the repertoire of monoclonal antibodies grows, the number of subpopulations also increases, and both elucidates and makes more complex our knowledge of the immune system. Despite their biological specificity, monoclonal antibodies for lymphocyte identification are costly. When flow cytometry is used, identification of lymphocyte subpopulations remains a labor intensive and time consuming test. Furthermore, conventional cytochemical stains, such as the reactions for nonspecific esterase and acid phosphatase activities, fail to demonstrate consistent differences in staining patterns between T helper and T suppressor cells; see Armitage, R. J., Linch, D. C., Worman, C. P. and Cawley, J. C.; The morphology and cytochemistry of human T-cell subpopulations defined by monoclonal antibodies and Fc receptors, British Journal of Haematology 51:605-613, 1982 and DeWaele, M., DeMey, J., Moeremans, M., Smet, L., Broodtaerts, L, and Van-Camp, B. and Cytochemical profile of immunoregulatory T-lymphocyte subsets defined by monoclonal antibodies Journal of Histochemistry and Cytochemistry 31:471-478, 1983. For these reasons investigation continues to be devoted to finding means by which these functionally defined populations can be distinguished and counted, with the expectation that measuring changes in these populations can lead to means of diagnosing, prognosticating, and following immune-mediated disorders.

Along these lines, an asymmetrical polymethine textile dye was developed into a stain for lymphocyte subpopulations using darkfield illumination; see Kass, L. Identification of lymphocyte subpopulations with a polymethine dye in the Journal of Histochemistry and Cytochemistry 36:711-715, 1988 and U.S. Pat. No. 4,810,487. Using this stain on a slide containing blood cells fixed in FAA (formalin, acetic acid, and 95% ethyl alcohol) and viewed under darkfield, T helper cells stained bright red, T suppressor cells were yellow-orange, B cells were yellow and contained yellow annular structures, and NK cells appeared green and contained prominent green granules.

Kass also disclosed that an oxazine textile dye (C.I. basic blue 141) can be used as a selective stain for neutrophils. Using an alkaline buffered solution of this stain applied to blood cells fixed in FAA fixative, the neutrophil granules stained bright crimson. The lymphocytes displayed pale green to blue green nuclei, but the cytoplasm was unstained. However, lymphocytes of different colors were not recognized; see Kass, Identification of neutrophils with an oxazine dye in the American Journal of Clinical Pathology 88:436-441, 1987. More recently, C.I. basic blue 141 was used in a buffered alkaline aqueous solution as the second reagent in a two-step stain for monocytes; see Kass, A two-step stain for monocytes using two different dyes applied in sequence (Biotechnic and Histochemistry 67:68-72, 1992).

It is evident from the state of the art that the identification and enumeration of the subpopulations of lymphocytes including the T-cells and B-cells, which are the major lymphocyte populations in man, are basic to the understanding of the immune system and the various diseases such as lymphoma, leukemias, and immunodeficiency problems. For example, B-cells represent about 10-20% of the peripheral blood lymphocytes. T-cells which are indicators of the cellular immune responses, i.e., delayed hypersensitivity and organ transplant rejection, constitute about 70-80% of the total. The lymphocyte subpopulations known as T-helper cells and T-suppressor cells, serve to regulate the antibody production and are effectors of T-cell functions. The enumeration of T-lymphocytes has diagnostic significance in certain chronic disorders where reduced numbers are found. Thus, monitoring the number of T-suppressor and T-helper cells has advanced the understanding and treatment of diseases affecting the immune system.

In accordance with this invention, crimson colored granules were made visible by a unique two-stage reaction using the stain in both the fixative and in the aqueous phases. It was found that staining occurred in T cytotoxic/suppressor cells and formed the basis for their identification and distinction from other forms of lymphocytes. The methods set forth in the above-mentioned Kass publications for obtaining coloration of the cells, required that the cells be first fixed in absolute alcohol with no stain and then stained with an aqueous buffer solution and rinsed in an aqueous solution contain metal cations with no buffer. In comparison, the colored photomicrograph of FIG. 1 shows that when peripheral blood was stained in accordance with the method of this invention, that the small dark-blue cells (nucleus and cytoplasm are both dark-blue) were identified as T-helper cells (CD4 cells). The cells with green nuclei and small maroon granules in the cytoplasm are T-cytoxic (suppressor CD8) cells and the cells with irregular blue nuclei and many red granules are neutrophils. Therefore, with a colored photomicrograph of FIG. 1, one would be able to clearly identify and therefore enumerate the lymphocytes among a plurality of other cells of hematopoietic origin.

SUMMARY OF THE INVENTION

This invention relates to a method and the stained cells derived therefrom for differentiating, identifying and enumerating cells and particularly human cells from each other among a plurality of cells of hematopoietic origin selected from the group consisting of blood cells, bone marrow cells, and lymph node cells. Preferably, the method comprises staining a biopsy specimen of hematopoietic origin, i.e., lymphocyte subpopulations from blood with a staining amount, e.g., up to 10 percent by weight of a specific oxazine dye in combination with a fixative, e.g., a solution of an alcohol, and then continuing to subject the stained cells to an aqueous alkaline solution containing small but staining amounts of the same oxazine dye. Subsequently, the stained cells, e.g., stained blood cells are treated with an effective amount of a specific buffer reagent (HEPES) in a substantially neutral aqueous solution which contains small but effective amounts, of up to about 1.0 percent and preferably from about 0.0001 to 0.1% or 0.0001 to 0.01% by weight of certain metal ions, such as metal ions of metal salts or other substantially water-soluble metal compounds. The lymphocyte subpopulations stained with the oxazine dye in accordance with this invention have individual color charateristics which enable the cells to be differentiated and enumerated, one from the other, by use of an instrument, e.g., microscope, etc.

More specifically, this invention relates to a method for differentiating, identifying and enumerating lymphocytes among a plurality of cells of hematopoietic origin comprising blood cells, bone marrow cells and lymph node cells which comprises:

(a) staining a biopsy specimen of said cells with a staining amount of an oxazine dye in the presence of a fixative, (b) continue staining said stained cells with a staining amount of the same oxazine dye in an alkaline aqueous solution, and (c) subsequently treating said stained cells with an effective amount of a substantially neutral buffer solution comprising (N-[2-hydroxyethyl]piperazine-N-[2-ethanesulfonic acid]) to obtain a plurality of stained cells having color characteristics that differentiate the lymphocytes from a plurality of the other stained cells; said neutral buffer solution containing water-soluble metal compounds selected from the group consisting of sodium, potassium, iron, calcium, magnesium, manganese and cadmium compounds; each of said metal compounds being present in said buffer solution in amounts ranging from about 0.0001 to 0.1 percent by weight of the solution.

Accordingly, it is an object of this invention to provide a single, substantially pure, oxazine dye for staining cells of hematopoietic origin for the identification and enumeration of lymphocyte subpopulations.

It is another object of this invention to provide a method of using a single dye capable of staining lymphocyte subpopulations of hematopoietic origin which can be viewed with a light microscope for identification and enumeration of each cell.

It is another object of this invention to provide stained cells of hematopoietic origin, and more particularly stained lymphocyte subpopulations of hematopoietic origin having individual color characteristics which permit the differentiation, identification and enumeration of said cells.

It is a further object of this invention to provide a method of staining a plurality of cells of hematopoietic origin by reacting a single oxazine dye with a biopsy specimen to obtain a plurality of stained cells having individual color characteristics which permit the differentiation, identification and enumeration of said cells.

These and other objects of the invention will become apparent from a further and more detailed disclosure of the invention.

In general, the invention relates to a rapid staining technique for lymphocyte populations, e.g., blood cells discernable under an ordinary light microscope. The method comprises the use of a fixative in combination with the dye, e.g., an alcohol solution of oxazine dye, i.e., basic blue 141, followed by continuing to subject the stained cells to an aqueous alkaline solution which also contains small but effective amounts of the same dye. Alternatively, the cells of hematopoietic origin can be stained with effective amounts of a solution of the dye in a fixative, e.g., an alcohol solution in combination with an aqueous alkaline solution of the same oxazine dye. Subsequently, the stained cells are treated, e.g., rinsed or washed with a substantially neutral HEPES buffer solution which contains small but effective amounts of specific metal ion, e.g., ions of metal salts to obtain a difference in the coloration of the lymphocytes. When correlated with cell sorter experiments wherein purified populations of T4 and cytotoxic-suppressor (CD8) were stained, the lymphocytes differed in both size and color. T helper cells were small and displayed deep blue nuclei and cytoplasm. T cytotoxic suppressor cells were larger than T helper cells, and exhibited pale green nuclei and cytoplasm, and a characteristic cluster of "smudge" of metachromatically staining crimson granules at or near the nuclear indentation.

These differences in color and size were pronounced. As a result, it was possible to count 100 lymphocytes in a buffy coat preparation in less than 5 minutes. Using an ordinary hand counter, it was easy to enumerate "dark blue lymphocytes" as well as "larger green lymphocytes with crimson granules." The absolute numbers of these lymphocytes could be expressed in various ways, such as the percentage dark blue lymphocytes (T helper cells) as a portion of the total number of lymphocytes counted, or as a ratio between the dark blue lymphocytes and the larger green lymphocytes with clustered crimson granules to approximate a helper/suppressor ratio. If buffy coats are not used, the oxazine stain can be used on a peripheral blood smear, recognizing that it may take a longer time to count cells than if a cell rich suspension were used. Peripheral venous blood samples can be obtained by direct capillary puncture and in evacuated EDTA tubes. Smears and coverslip preparations were made from both types of samples and air dried. Buffy coat preparations were made from leukocyte-rich plasma after gravity sedimentation of erythrocytes in the blood collection tube.

For the oxazine dye, i.e., basic blue 141, there exists a relationship between the molecular structure of the dye and its ability to stain lymphocytes differentially, under the conditions of the staining procedure described by this invention. Basic blue 75, for example, which lacks a methyl group on the benzine ring shows inconsistent and poor differential coloration of lymphocytes when compared with basic blue 141. Reasons why the methyl group on the benzine ring confers the selective staining property are not understood. However, studies with other dyestuffs have demonstrated similar selective staining properties that appear to be related to small differences in molecular structures; see Kass, L. basic blue 41: A new panoptic stain for blood and bone marrow cells Journal of Histotechnology 11:10–14, 1988 and U.S. Pat. No. 4,714,606.

As shown in the specific examples, the substantially neutral metal complex-buffer solution comprising certain metal ions, e.g., derived from metal salts and HEPES (N-[2hydroxyethyl]piperazine-N-[2-ethanesulfonic acid] produced the most intense colors in lymphocytes, and the least amount of "bleeding" of the reaction product and background discoloration. When compared with (1) the HEPES buffer solution alone or (2) with HEPES with each of the individual metal salts, the HEPES buffer and metal ions solution of this invention produced the maximum differences in colors of the various lymphocytes, thereby facilitating visual discriminations between T helper and T cytotoxic suppressor cells.

For example, in many immunopathology and hematology laboratories, identification of lymphocyte subpopulations has become a routine and in some instances a daily procedure. With highly specific monoclonal antibodies and flow cytometry or fluorescence microscopy, identification of T helper, T suppressor, T cytotoxic suppressor, NK or natural killer, and other subpopulations can be achieved. In the laboratory of today, confined by ever increasing cost restraints, identifications of lymphocyte subpopulations using monoclonal antibodies and flow cytometry is an expensive, labor intensive, and time consuming procedure. Thus, a less expensive, faster means of identifying these subpopulations than that available with current reagents and technologies is needed.

For these reasons, a wide variety of textile dyestuffs were screened as possible reagents for lymphocyte subpopulation identification under the conventional light microscope. Of the many different dyes tested under a variety of conditions of fixation and buffering, one dye emerged as the dye that could distinguish between T helper cells and T suppressor cells on the basis of differences in color. Specifically, this dye is 3-(2-methylphenylamino)-7-(N,N-diethylamino)-phenoxyazin-5-ium chloride, known as C.I. basic blue 141 (oxazine dye) having the formula:

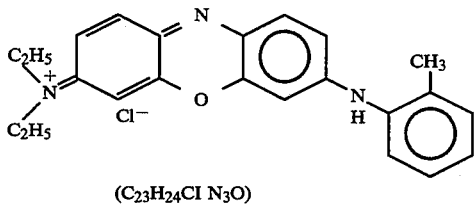

($C_{23}H_{24}Cl\ N_3O$)
Structural formula of C.I. basic blue 141.
3-(2-methylphenylamino)-7-
(N,N-diethylamino)-phenoxyazin-5-ium chloride

DETAILED DESCRIPTION

Peripheral venous blood samples were obtained from several presumed normal persons in evacuated tubes containing EDTA (ethylenediamine tetraacetic acid) as an anticoagulant, and in separate tubes containing heparin. From each person, one 7 ml tube containing blood and EDTA was allowed to stand upright at room temperature for one hour, to permit gravity sedimentation of erythrocytes. Alternatively, a single 7 ml tube of anticoagulated blood was centrifuged at 2500 rpm for 5 minutes at room temperature to obtain a buffy coat layer.

In the example of the gravity sedimented tube, leukocyte rich plasma was removed with a Pasteur pipette, placed in a separate tube, and centrifuged at 2500 rpm for 5 minutes to obtain a button of cells composed largely of leukocytes, platelets, and erythrocytes. All but 100 microliters of the supernatant plasma was removed with a Pasteur pipette, and the button was resuspended using a Vortex Genie mixer. From the centrifuged tube of whole blood, the buffy coat layer was removed with a Pasteur pipette and placed into a separate tube. From tubes containing either the leukocyte rich suspension obtained by centrifugation of leukocyte rich plasma after sedimentation of erythrocytes, or buffy coat obtained by centrifugation of whole blood, thin smears were made on methanol cleaned glass coverslips or slides and air dried.

For flow cytometry, 40 ml heparinized peripheral venous blood was obtained from several presumed normal persons, and layered over Ficoll-Hypaque to separate a lymphocyte rich fraction from other cells. Several drops of this fraction were used to prepare coverslip films, and were stained in the manner described herein. The remainder of the fraction was sorted in a cell sorter using CD4/CD8 monoclonall antibody reagent (BD Immunocytochemistry, San Jose, Calif.) to separate T helper cells from T suppressor cells. The sorted cell populations were 98–99% pure as a single cell type. For the T suppressor cell fraction, only the most brightly fluorescent cells outlined by the gate were collected. These cells were largely T cytotoxic suppressor cells. The other less brightly fluorescent cells in the CD8 fraction were a mixture composed largely of NK cells and lesser numbers of T suppressor cells. The sorted populations were collected in 10×75 mm plastic tubes and centrifuged for 10 minutes at 2500 rpm. All but 50 microliters of the supernatant plasma was removed, and aliquots of the cell suspension were placed in a cytocentrifuge. Cytospin specimens were air dried and stored at room temperature.

STAINING PROCEDURE WITH OXAZINE DYE (BB141) COMPRISES: REAGENTS

1. Solution A (Dye and Fixative Mixture): 5% solution of oxazine dye (C.I. basic blue 141 from BASF, Whippany, N.J.) was prepared in absolute methanol as the fixative and centrifuged for 10 minutes at 2500 rpm. The supernatant was kept in a tightly stoppered bottle at room temperature. This solution was stable with no visible change in staining properties for one year. The solution may contain up to about 10 percent by weight of the dye, e.g., 0.01 to 5.0 percent in a low molecular weight $C_1$–$C_4$ alcohol.

2. Solution B: 2.5% aqueous solution of oxazine dye (C.I. basic blue 141) was prepared by adding distilled water to the powdered dye. The solution was centrifuged for 10 minutes at 2500 rpm. The supernatant was placed in a tightly stoppered bottle at room temperature. The solution did not show any diminution of staining properties up to one year. The aqueous solution may contain up to about 5 percent by weight of the dye, e.g., 1.0 to 5.0 percent.

3. Solution C: Trizma maleate, pH 7.6 buffer concentrate, was prepared by placing 47.44 grams Trizma maleate (Sigma, St. Louis) in a one liter graduated cylinder. Distilled water was added to make 950 ml. It was placed in a large beaker and the pH of the solution was adjusted to 7.6 with dropwise addition of concentrated NaOH, stirring constantly. The volume was increased to one liter with distilled water in a one liter graduated cylinder. 10 drops of liquid phenol was added as a preservative, and stored tightly stoppered in the refrigerator at 5 degrees C. The buffered solution was stable for one year without deterioration. Effective amounts of various known buffers, e.g., 0.001 to 1.0 percent by weight may be used in preparing the aqueous alkaline solution.

4. Solution D: A final treatment, i.e., rinse metal complex buffer solution was prepared in the following manner. All of the metal salts from Table I were used in combination with the aqueous solution of the HEPES buffer. The pH was adjusted to 7.0 by adding NaOH to the solution.

TABLE I

| Metal Salts | Amount in one liter of $H_2O$ |
|---|---|
| cadmium acetate | 36 mg |
| manganese chloride | 23 mg |
| potassium acetate | 2510 mg |
| ferric chloride | 5 mg |
| calcium chloride $2H_2O$ | 330 mg |
| sodium chloride | 178 mg |
| HEPES | 1.19 grams |
| magnesium chloride | 3.35 mg |

HEPES (N-[2-hydroxyethyl] piperazine-N-[2-ethanesulfonic acid])

As a specific example for preparing solution D, to one liter of 100× concentrate, 10 drops of liquid phenol was added and stored in the refrigerator at 5 degrees C. To prepare a 1× working buffer, 10 ml of the 100× concentrate was added to a one liter plastic or glass bottle, and then 990 ml of distilled or deionized water was added. Preferably, the staining procedure comprises placing slides containing buffy coat on a staining pan and flooding the surface with effective amounts of Solution A. An effective amount includes a staining amount ranging up to about 10 percent by weight of the dye in the alcohol fixative, e.g., from 0.01 to 5.0 percent in $C_1$-$C_4$ alcohols. During the five minute period of staining with Solution A, Solutions B and C were prepared as follows: Four ml of Solution B was added to test tube and to it four ml of Solution C was added. The addition of Solution C to Solution B caused the solution to change color from bright blue to purple. This solution is stable at room temperature for 24 hours without visible deterioration of staining properties. After about five minutes of staining time with Solution A, Solutions B and C are added directly on top of the surface of Solution A by dropwise addition with a Pasteur pipette. This step effects an admixture of the Solutions A, B and C. The addition of Solutions B and C causes a golden sheen to form on the surface of the liquid. Subsequently, after about 5-10 minutes, allowing excess stain to drain, the slides were rinsed by vigorous agitation in a 100 ml beaker containing Solution D for about 10-15 seconds. Solution D can be used on 30 coverslips or 15 slides, if kept covered at room temperature.

For comparison, three different lots of basic blue 141 were tested. To enhance visual perception of red colors, and heighten the contrast between blue and green, a didymium filter was placed over the light source of the microscope and any blue filter was removed. Cells were photographed with a Zeiss Axioskop using Kodak Tungsten 64 Professional color film, and processed to heighten contrast. As a part of the experiment, a variety of oxazine dyes that have been used as biological stains were screened to investigate whether any of them displayed differential coloration of lymphocytes in the same degree as basic blue 141. The dyes tested included Capri blue, brilliant cresyl blue, resazurin, resorcein, orcein, modern violet N, gallocyanin, gallo blue E, gallamin blue, celestin blue, darrow red, nile blue 2B, cresyl violate acetate, cresyl fast violet, nile blue, rhodanile blue, Meldola's blue, basic blue 3, and delphine blue. With the exception of basic blue 3 (Mobay, Pittsburgh), all of these stains were obtained from Gurr (London) or Chroma (Leipzig).

Moreover, virtually all of the currently available oxazine textile dyes as well as several obsolete oxazine textile dyes were tested in a manner identical to that of basic blue 141, to ascertain whether any of these dyes yielded similar staining results. These other dyes similar to BB-141 included Basacryl blue X4-GFL (basic blue 122, BASF, Whippany, N.J.), Sevron pure blue 4G (basic blue 87, Crompton and Knowles, Charlotte, N.C.), Sevron pure blue 4G (basic blue 87, Crompton and Knowles, Charlotte, N.C.), Remacryl dark blue EGRL (Hoechst, Somerville, N.J.), Remacryl blue G (basic blue 96, Hoechst), Remacryl blue B (basic blue 95, Hoescht), Remacryl blue 4RL (basic blue 148, Hoechst), and Astrazon blue 9GL (basic blue 75, Mobay, Pittsburgh, Pa.). Of all these dyes, basic blue 75 (Astrazon blue GL) was the only dye that had a molecular structure resembling that of basic blue 141. Basic blue 141 differs from basic blue 75 by a single methyl group on the benzene side ring.

Additional tests of the final rinse HEPES buffer solution were also undertaken to ascertain which component or components of the metal complex-buffer solution described herein were responsible for optimal developments of the characteristics colors in lymphocytes. For these experiments, the following solutions were prepared: HEPES plus cadmium acetate, HEPES plus ferric chloride, HEPES plus manganous chloride, HEPES plus calcium chloride, HEPES plus sodium chloride, and HEPES plus magnesium chloride. Concentrations of the metal salts and HEPES were identical to solutions used in the metal complex buffer solution shown in Table I. As a control, HEPES buffer solution alone without any metal ions, i.e., metal salts was used. Coverslip preparations of buffy coat were stained in the manner described for this invention, and rinsed separately so that a single coverslip was exposed to only one of the buffer-metal salt solutions. In this way, a series of coverslips were stained and rinsed, each in a different buffer-metal salt solution. In testing these different buffer solutions, the buffy coat preparations from peripheral venous blood samples obtained from normal persons, showed lymphocytes of various sizes and colors. Most of the lymphocytes, ranging from 50-70% of the total number of lymphocytes, displayed a distinctive dark blue nucleus and dark blue cytoplasm. Occasionally, a few red or purple punctate structures were seen in the nucleus and cytoplasm. Compared with the abundant dark blue stained small lymphocytes, other lymphocytes were fewer in number and had different color properties. In this second population, lymphocytes appeared larger than the small, dark blue stained lymphocytes. In this smaller population, lymphocytes displayed pale blue green or green nuclei, pale green cytoplasm, and a cluster of crimson colored metachromatically staining granules near the indentation of the nucleus.

Often, variable numbers of these structures were seen throughout the cytoplasm. In some instances, the granules appeared to coalesce, forming a "smudge." Rarely, large lymphocytes were detected, and usually showed pale green nuclei with a large number of metachromatically staining crimson granules clustered near the nuclear indentation.

Neutrophils contained pale staining crimson granules, basophil granules were blue to purple, eosinophil granules were stained orange, and monocytes exhibited pale lavender cytoplasm often containing dustlike metachromatically staining pink or crimson granules. Nuclei of these cells were pale lavender to pale blue. Erythrocytes were largely unstained, and platelets showed blue cytoplasm and pink to purple granules. In coverslip preparations of Ficoll-Hypaque gradients, lymphocytes of varying sizes and shapes were seen. Small lymphocytes that displayed dark blue nuclear staining predominated in this fraction. Other lymphocytes appeared larger than the small dark blue lymphocytes, and showed pale green nuclei and blue cytoplasm. Approximately 20-30% of these cells also contained 10-20 magenta granules in the cytoplasm. Large lymphocytes with coarse magenta granules were seen rarely, as were monocytes and eosinophils.

In the cytospin preparations of cell sorts, T helper cells (CD4) displayed dark blue nuclei and dark blue cytoplasm. Rarely, a few crimson colored punctate structures were seen in the nucleus or in the cytoplasm. In T cytotoxic suppressor cells (CD8), the nuclei were pale blue to blue green, and the cytoplasm was pale green. Invariably, there was a cluster of metachromatically staining granules or a "smudge" representing a cluster of these granules, at or near the nuclear indentation. Often, a few of these granules were scattered throughout the cytoplasm. Rarely, a monocyte was seen in the CD8 sort. For the most part, CD8 lymphocytes were larger than CD4 lymphocytes. Both lots of basic blue 141 gave essentially the same staining results.

In the experiments designed to elucidate the components of the metal-complex buffer solution, responsible for color development, the HEPES buffer alone as well as the HEPES-individual metal salt solutions produced good results. However, the important differences in color between the T helper and T cytotoxic suppressor cells were substantially more pronounced when the stained cells were treated, with the complex metal-HEPES solution of this invention wherein all of the metal ions, e.g., metal salts were present in comparison to the buffer solutions containing only HEPES or HEPES with only one or two of the metal salts. In the HEPES buffer alone as well as the HEPES plus only some of the individual metal salts, the coverslips displayed a bright crimson "bleeding" of reaction product when a toluene or xylene based resin mounting medium was used. The coverslips rapidly attained a crimson color, particularly at the edges, and under the microscope the background appeared pink to rose colored. However, in the coverslips rinsed with the complex metal-buffer solution containing all of the metals and HEPES, this crimson "bleeding" was inconspicuous or did not appear at all particularly when the cyanoacrylate adhesive was used.

While these results may not be completely understood, it is believed that the metal ions of the salts in the aqueous solution of buffer reagent forms a metal complex with the oxazine molecule and the stained blood cells during the subsequent treatment, i.e., rinse stage to enhance the color characteristics of the stained cells. For purposes of this invention, the metal ions of the metal salts or compounds include metals selected from Groups I, II, III, VII and VIII of the Periodic Table as set forth in the CRC Handbook of Chemistry and Physics, 64th Edition (1983-1984) by R. C. Weast et al. Moreover, of all of the oxazine dyes tested, only the basic blue 141-metal complex gave consistent and differential coloration of lymphocytes. For example, with basic blue 75, a dye closely resembling basic blue 141, but differing by lack of a methyl group on the benzene ring, differential staining of lymphocytes occurred inconsistently, and was considerably less pronounced than that obtained with basic blue 141.

The fixatives which may be utilized for fixing the biopsy specimens in accordance with this invention, are generally well known in the art and include the alcohols such as methanol or ethanol, formaldehyde and the like. In general, fixing the biopsy specimens or tissue is accomplished by using a neutral buffered solution of formalin or absolute alcohol such as methanol. A buffered solution of formalin is a general purpose fixative. Fixatives useful for purposes of this invention, e.g., staining of biopsy specimens, may be found in the text by S. W. Thompson and R. D. Hunt entitled, "Selected Histochemical Histopathological Methods," published by Charles C. Thomas, Springfield, Ill.

While this invention has been described by a number of specific examples, it is obvious that there are other variations which can be made without departing from the spirit and scope of the invention as particularly set forth in the appended claims.

The invention claimed is:

1. A method for differentiating, identifying and enumerating lymphocytes among a plurality of cells of hematopoietic origin comprising blood cells, bone marrow cells and lymph node cells which comprises:
   (a) staining a biopsy specimen of said cells with a staining amount of an oxazine dye in solution with a fixative;
   (b) continue staining said stained cells with a staining amount of the same oxazine dye in an alkaline aqueous solution; and
   (c) subsequently treating said stained cells with an effective amount of a substantially neutral buffer solution of (N-[2-hydroxyethyl]piperazine-N-[2-ethanesulfonic acid]) to obtain a plurality of stained cells having color characteristics that differentiates the lymphocytes from a plurality of the other stained cells; said neutral buffer solution containing substantially water-soluble metal compounds selected from the group consisting of sodium, potassium, iron, calcium, magnesium, manganese and cadmium; said metal compounds being present in said buffer solution in an amount ranging from about 0.0001 to 0.1 percent by weight of the solution; said oxazine dye having the formula:

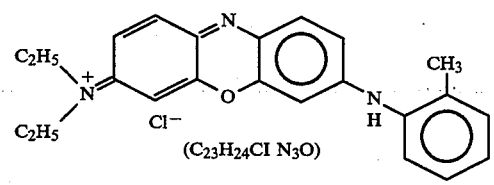

($C_{23}H_{24}Cl\,N_3O$)

2. The method of claim 1 wherein the oxazine dye is in solution with the fixative in amounts ranging from 0.01 to about 5.0 percent by weight.

3. The plurality of stained cells obtained by the method of claim 1 comprising stained lymphocyte subpopulations.

4. A method for differentiating, identifying and enumerating lymphocytes among a plurality of cells of hematopoietic origin comprising blood cells, bone marrow cells and lymph node cells which comprises:

(a) staining a biopsy specimen of said cells with a staining amount of an oxazine dye in solution with an alcohol fixative;

(b) continue staining said stained cells with a staining amount of the same oxazine dye in an alkaline aqueous solution; and (c) subsequently treating said stained cells with an effective amount of a substantially neutral buffer solution of N-[2-hydroxyethyl]piperazine-N-[2-ethanesulfonic acid] to obtain a plurality of stained cells having individual color characteristics that differentiates the lymphocytes from one another and from a plurality of the other stained cells; said neutral buffer solution containing water-soluble metal compounds selected from the group consisting of sodium, potassium, iron, calcium, magnesium, manganese and cadmium; each of said metal compounds being present in said buffer solution in amounts ranging from about 0.0001 to 0.01 percent by weight of the solution; said oxazine dye having the formula:

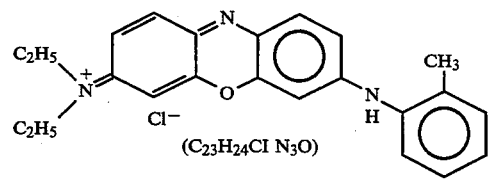

5. The process of claim 2 wherein the cells are stained with a solution of the fixative and the oxazine dye wherein the fixative is a lower molecular weight aliphatic alcohol of one to four carbons.

6. The method of claim 4 wherein the stained lymphocytes have color characteristics which are differentiated, identified and enumerated with a microscope.

7. The method of claim 4 wherein the neutral buffer solution contains the metal compounds of sodium, potassium, iron, calcium, magnesium, manganese and cadmium in an amount ranging from 0.001 to about 0.1 percent by weight.

8. The method of claim 4 wherein the stained cells are treated with the solution of N-[2-hydroxyethyl]piperazine-N-[2-ethanesulfonic acid] for a period ranging from about 10 to 15 seconds.

9. The method of claim 4 wherein the cells of hematopoietic origin are blood cells.

10. The method of claim 9 wherein the cells of hematopoietic origin are cells having a subpopulation comprising T-helper cells, T-suppressor cells, B-cells, Natural Killer cells, eosinophils, basophils, neutrophils, monocytes, and platelets.

* * * * *